United States Patent [19]

Nickell et al.

[11] Patent Number: 4,615,728
[45] Date of Patent: Oct. 7, 1986

[54] PYRIDINYLOXY PROPOINAMIDE DERIVATIVES USEFUL IN INCREASING THE RECOVERABLE SUGAR IN SUGARCANE

[75] Inventors: Louis G. Nickell; Leonard J. Stach; Takeo Hokama, all of Chicago, Ill.

[73] Assignee: Sandoz Ltd., Basel, Switzerland

[21] Appl. No.: 766,473

[22] Filed: Aug. 19, 1985

[51] Int. Cl.⁴ .................... A01N 43/40; C07D 401/12
[52] U.S. Cl. ........................................ 71/94; 546/283
[58] Field of Search ............................. 546/283; 71/94

[56] References Cited

U.S. PATENT DOCUMENTS

| | | | |
|---|---|---|---|
| 3,996,234 | 12/1976 | Bossert et al. | 546/283 |
| 4,083,714 | 4/1978 | Takahashi et al. | 546/283 |
| 4,163,787 | 8/1979 | Malhatra et al. | 514/336 |
| 4,300,944 | 11/1981 | Böhner et al. | 546/283 |
| 4,325,729 | 4/1982 | Rempfler et al. | 546/283 |

Primary Examiner—Henry R. Jiles
Assistant Examiner—J. Richter
Attorney, Agent, or Firm—Gerald D. Sharkin; Richard E. Vila

[57] ABSTRACT

This invention relates to a propionamides of the following structural formula:

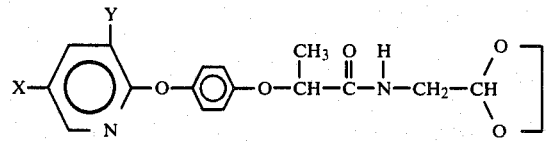

wherein X is chlorine or trifluoromethyl and Y is hydrogen or chlorine. The compounds of this invention are useful as sugarcane ripeners.

8 Claims, No Drawings

PYRIDINYLOXY PROPOINAMIDE DERIVATIVES USEFUL IN INCREASING THE RECOVERABLE SUGAR IN SUGARCANE

This invention relates to new propionamides having the structural formula:

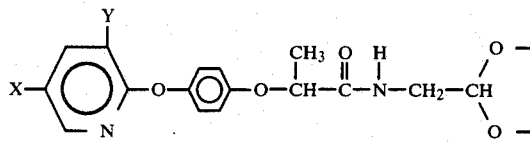

wherein X is chlorine or trifluoromethyl and Y is hydrogen or chlorine.

These compounds are particularly useful in increasing the recoverable sugar in sugarcane by treating the sugarcane plant during its maturation with a compound of the foregoing structural formula.

A variety of plant growth regulators, stimulants and promotors have been tried in the past in attempts to increase the yields of cultivated crops. It has been found that materials that have an effect on one crop will not necessarily have an effect or have a different effect on other crops.

One particular crop which has been given increased attention for the purpose of increasing yields is sugarcane. Accordingly it is an object of the present invention to provide new methods and compositions of increasing the yield of sugar obtained from sugarcane.

It has now been found that the recovery of sugar from sugarcane can be significantly increased by the use of certain propionamides. Consequently it has now been found that it is possible to increase the recoverable sugar in sugarcane by contacting the sugarcane plant with an effective amount of the aforedescribed propionamides.

The compounds of the present invention are readily prepared by reacting the corresponding acid chloride of the structural formula:

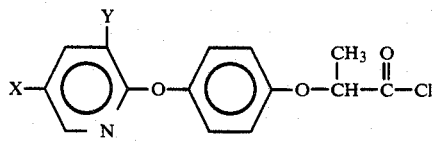

with 1,3-dioxolan-2yl-methylamine in the presence of an acid scavenger and an inert solvent as set forth in the following examples:

EXAMPLE 1

Preparation of N-(1,3-dioxolan-2-ylmethyl)-2-[4-(3,5-dichloro-2-pyridinyloxy)phenoxy]propionamide 2-[4-(3,5-Dichloro-2-pyridinyloxy)phenoxy]-propanoic acid (3.4 grams; 0.0104 mol) and thionyl chloride (12 ml) were placed into a 50 ml glass reaction flask equipped with stirrer, condenser, thermometer and nitrogen line. The mixture was stirred for 75 minutes at 70 C. Then the mixture was cooled and stripped. The desired acid chloride product was dissolved in toluene.

2-[4-(3,5-Dichloro-2-pyridinyloxy)phenoxy]-propanoic acid chloride (3.8 grams; 0.00115 mol) and 2-aminomethyl-1,3-dioxolane (1.2 grams; 0.00116 mol), triethylamine (5 ml) and toluene (110 ml) were placed in a glass reaction flask equipped with stirrer, condenser, thermometer and nitrogen line and stirred for two hours at room temperature. The flask was stoppered and stored at 0° C. It was then transferred into a separatory funnel at room temperature and washed three times with water (70 ml). Then the mixture was dried and stripped of solvent resulting in a off-white solid product (4.8 grams). This product was recrystallized from a mixture of methylene chloride and hexane. The first crop, a white solid, (2.4 grams) had a melting point of 127° C., analysis:

|  | Theoretical (%) | Found (%) |
| --- | --- | --- |
| Carbon | 52.31 | 52.02 |
| Hydrogen | 4.39 | 4.44 |
| Nitrogen | 6.78 | 6.64 |
| Chlorine | 17.16 | 17.43 |

Infrared analysis was consistent with the desired product.

EXAMPLE 2

Preparation of N-(1,3-dioxolan-2-ylmethyl)-2-[4-(5-trifluoromethyl-2-pyridinyloxy)phenoxy]propionamide 2-[4-(5-Trifluoromethyl-2-pyridinyloxy)phenoxy]-propanoic acid (21 grams; 0.064 mol) and thionyl chloride (34 ml) were placed into a glass reaction flask equipped with stirrer, thermometer and reflux condenser. The mixture was refluxed for 1.5 hours and stripped of excess thionyl chloride on a rotoevaporator leaving the desired acid chloride (22 grams) as a solid.

1,3-Dioxolan-2 ylmethylamine (4 grams; 0.04 mol), triethylamine (5 ml) and dichloromethane (150 ml) were placed in a 3-necked glass reaction flask equipped with stirrer, thermometer and reflux condenser and cooled to 5° C. 2[4-(5-Trifluoromethyl-2-pyridinyloxy)-phenoxy]-propanoic acid chloride (9 grams; 0.027 mol) in dichloromethane (30 ml) was added in a five minute time period. The reaction mixture was stirred for 1 hour at 5° C.-20° C., washed with water, passed through phase separating paper and concentrated to a dark gum (10.5 grams). The product was chromatographed through Florisil clay (100 ml), using hexane-ethyl acetate solvent mixtures. The desired product was isolated as a yellow gum (3.0 grams) and had the following elemental analysis:

|  | Theoretical (%) | Found (%) |
| --- | --- | --- |
| Carbon | 55.34 | 54.96 |
| Hydrogen | 4.64 | 4.81 |
| Nitrogen | 6.79 | 6.73 |

Infrared analysis was consistent with structure.

The effectiveness of the compounds of this invention for increasing the yield of sugar obtained from sugarcane is demonstrated by the following experiments. The cane was harvested 8 weeks after application of the compounds of Examples 1 and 2.

The top 14 joints of the treated cane as well as those of the controls were removed, combined and analyzed for juice purity and pol percent cane, following the "press method" developed and described by T. Tanimoto, Hawaiian Planters Record, 57, 133 (1964).

Pol percent cane is a polarmetric determination and equals the percentage of sucrose if the latter is the only substance in the solution which will rotate the plane of polarized light. The pol percent cane is a standard method of determining the sucrose content of sugarcane.

|  | Rate of Application (lbs. per acre) | Pol % Cane | Juice Purity |
|---|---|---|---|
| TEST 1 | | | |
| COMPOUND OF EXAMPLE 1 | 1 | 84.55 | 12.52 |
| CONTROL | 0 | 77.84 | 10.23 |
| TEST 2 | | | |
| COMPOUND OF EXAMPLE 1 | 1 | 86.72 | 13.56 |
| COMPOUND OF EXAMPLE 1 | 1 | 86.87 | 14.31 |
| CONTROL | 0 | 77.32 | 9.98 |
| TEST 3 | | | |
| COMPOUND OF EXAMPLE 1 | 1 | 84.63 | 13.18 |
| COMPOUND OF EXAMPLE 2 | 1 | 87.25 | 14.81 |
| CONTROL | 0 | 76.54 | 10.06 |
| TEST 4 | | | |
| COMPOUND OF EXAMPLE 2 | 1 | 86.46 | 14.25 |
| CONTROL | 0 | 80.66 | 11.61 |
| TEST 5 | | | |
| COMPOUND OF EXAMPLE 2 | 1 | 86.35 | 13.32 |
| COMPOUND OF EXAMPLE 2 | 0.5 | 87.37 | 14.15 |
| COMPOUND OF EXAMPLE 2 | 0.1 | 87.74 | 14.04 |
| CONTROL | 0 | 81.76 | 10.78 |

In the use of this compound to increase the recoverable sugar in sugarcane, sugarcane is treated at a late stage of development of the sugarcane wherein most of the sugar formation takes place. Thus, under normal growing conditions and common cultivation practices the active compound of this invention can be applied to the sugarcane during the period of from about 2 to about 10 weeks before harvesting.

The amount of active compound required to efectively increase the recoverable sugar from sugarcane can vary somewhat depending on such factors as the time of application, the weather, crop density, method of application and the like. Generally, an amount of at least 0.1 pounds per acre and preferably an amount of from 0.1 pounds per acre to about 10 pounds per acre can be used. While an amount greater than those mentioned can be used, they will now result in an advantage that would warrant their expense and are, therefore, not practical.

For practical use in treating sugarcane, the active compounds of this invention are generally incorporated into compositions or formulations which comprise an inert carrier and an effective amount of the compound. The compositions enable the active compound to be conveniently applied to the sugarcane at the desired rate. The formulations can be liquid formulations such as emulsifiable concentrates or solutions or solid formulations such as dusts, granules or wettable powders.

The preferred compositions are liquid formulations, particularly solutions or emulsifiable concentrates. Emulsifiable concentrates comprise the active compound, according to this invention, and as the inert carrier, a solvent and an emulsifier. Such emulsifiable concentrates can be extended with water and/or oil to any desired concentration of active compound for application as sprays to the sugarcane. The emulsifier most commonly used in these concentrates are nonionic or mixtures of nonionic with anionic surface-active agents. With Ohe use of some emulsifier systems an inverted emulsion (water-in-oil) can be prepared.

Typical formulations according to the present invention useful for increasing the recoverable sugar in sugarcane are illustrated in the following examples wherein the quantities are given in parts by weight.

EXAMPLE 2

Preparation of an Emulsifiable Concentrate

The following ingredients are blended thoroughly until a homogeneous liquid concentrate is obtained. This concentrate is mixed with water to give an aqueous dispersion containing the desired concentration of the active ingredients for use as a spray.

| Product of EXAMPLE 1 | 25 |
|---|---|
| Sodium lauryl sulfate | 2 |
| Sodium lignin sulfate | 3 |
| Kerosene | 70 |

EXAMPLE 3

Preparation of a Wettable Powder

The following components are mixed intimately in conventional mixing or blending equipment and are then ground to a powder having a particle size of les than about 50 microns. The finished powder is dispersed in water to give the desired concentration of active compound for application to the sugarcane.

| Product of EXAMPLE 2 | 50 |
|---|---|
| Fuller's earth | 47 |
| Sodium lauryl sulfate | 2.5 |
| Methyl cellulose | 0.5 |

EXAMPLE 4

Preparation of a Dust

The following ingredients are mixed thoroughly and are then ground to an average particle size of less than about 50 microns to give a dust suitable for application with conventional dusting equipment.

| Product of EXAMPLE 1 | 10 |
|---|---|
| Powdered talc | 90 |

The effectiveness of the compounds of this invention for increasing the recoverable sugar from sugarcane was demonstrated in a field test by applying a solution in acetone diluted for application to the various indicated application rates. The test compound was applied at each rate on the spindle area of each of 20 stalks of sugarcane in a field in Hawaii, using a syringe with a fine needle as the applicator. A set of 10 of these treated stalks from each group was harvested at 4 and 8 weeks after such treatment. In each harvest a set of 10 untreated stalks were also harvested as a control.

We claim:

1. A compound of the formula:

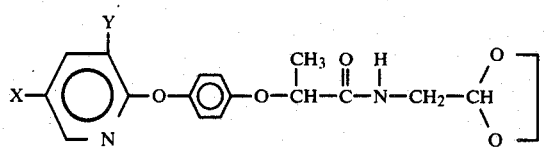

wherein

X is chlorine or trifluoromethyl

Y is hydrogen or chlorine.

2. The compound of claim 1, N-(1,3-dioxolan-2-ylmethyl)-2-[4-(5-trifluoromethyl-2-pyridinyloxy)phenoxy]-propionamide.

3. The compound of claim 1, N-(1,3-dioxolan-2-ylmethyl)-2-[4-(3,5-dichloro-2-pyridinyloxy)phenoxy]propionamide.

4. A method for increasing the recoverable sugar contained in sugarcane which comprises contacting the sugarcane plant with an effective amount of a propionamide of claim 1.

5. The method of claim 4 wherein the propionamide is N-(1,3-dioxolan-2-ylmethyl)-2-[4-(5-trifluoromethyl-2-pyridinyloxy)phenoxy]propionamide.

6. The method of claim 4 wherein the propionamide is N-(1,3-dioxolan-2-ylmethyl)-2-[4(3,5-dichloro-2-pyridinyloxy)phenoxy]propionamide.

7. The method of claim 4, 5 or 6 wherein the sugarcane is contacted with from about 0.1 to about 10 pounds per acre of the ester.

8. The method of claim 4, 5, 6 or 7 wherein the sugarcane is contacted with the ester during the period of from about 2 to about 10 weeks before harvest.

* * * * *